US00PP32383P2

(12) United States Plant Patent
Heuger

(10) Patent No.: US PP32,383 P2
(45) Date of Patent: Oct. 20, 2020

(54) ***HELLEBORUS* PLANT NAMED 'COSEH 6900'**

(50) Latin Name: ***Helleborus niger* X *Helleborus* x *hybridus***
Varietal Denomination: COSEH 6900

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/602,736

(22) Filed: Nov. 29, 2019

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

(56) References Cited

PUBLICATIONS

PLUTO UPOVROM Plant Variety Database Citation for 'COSEH 6900' as per QZ PBR 20183167; Feb. 16, 2019; 1 page.*

* cited by examiner

*Primary Examiner* — Kent L Bell
(74) *Attorney, Agent, or Firm* — C. A. Whealy

(57) ABSTRACT

A new and distinct cultivar of *Helleborus* plant named 'COSEH 6900', characterized by its upright and mounded plant habit; moderately vigorous to vigorous growth habit; dark green-colored leaves; freely flowering habit; single light yellow green-colored flowers; and good garden performance.

2 Drawing Sheets

Figure 1:
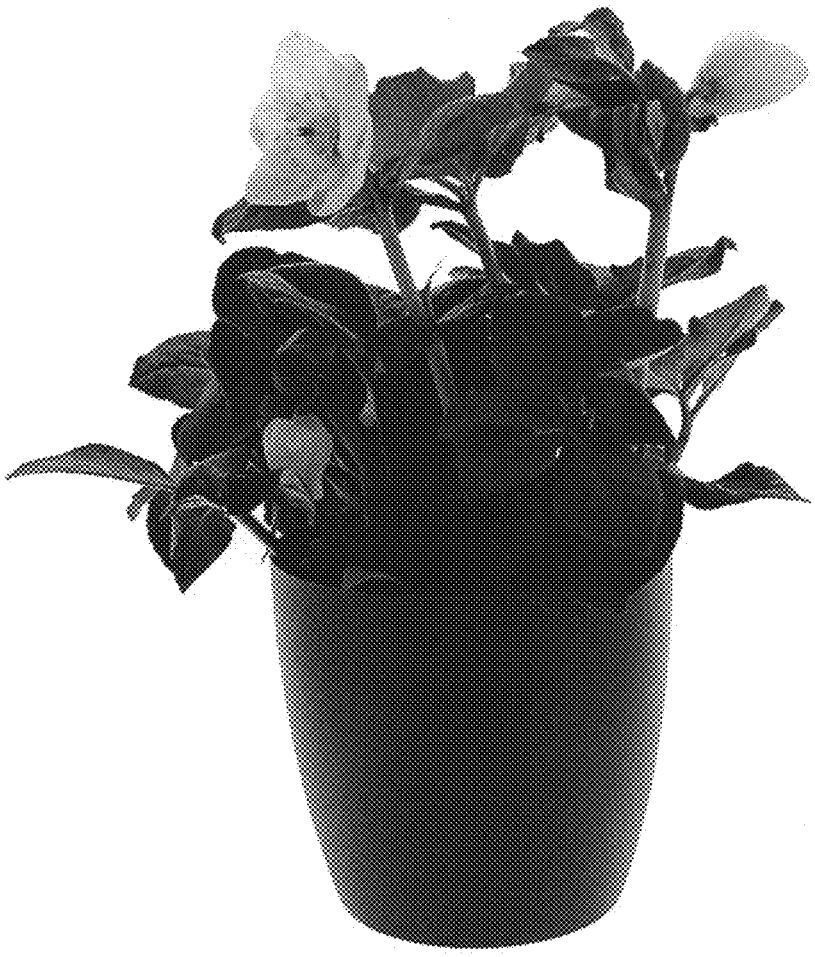

Botanical designation: *Helleborus niger* X *Helleborus* x *hybridus*.

Cultivar denomination: 'COSEH 6900'.

CROSS-REFERENCED TO CLOSELY-RELATED APPLICATIONS

Title: *Helleborus* Plant Named 'COSEH 5600'
Applicant: Josef Heuger
Filed: Concurrently with the instant application Ser. No. 16/602,791

Title: *Helleborus* Plant Named 'COSEH 5700'
Applicant: Josef Heuger
Filed: Concurrently with the instant application Ser. No. 16/602,738

Title: *Helleborus* Plant Named 'COSEH 5900'
Applicant: Josef Heuger
Filed: Concurrently with the instant application Ser. No. 16/602,735

Title: *Helleborus* Plant Named 'COSEH 7100'
Applicant: Josef Heuger
Filed: Concurrently with the instant application Ser. No. 16/602,734

Title: *Helleborus* Plant Named 'COSEH 7500'
Applicant: Josef Heuger
Filed: Concurrently with the instant application Ser. No. 16/602,737

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 6900'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2011 of a unnamed selection of *Helleborus niger*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in November, 2013.

Asexual reproduction of the new *Helleborus* plant by divisions in a controlled environment in Glandorf, Germany since February, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 6900'. These characteristics in combination distinguish 'COSEH 6900' as a new and distinct *Helleborus* plant:

1. Upright and mounded plant habit.
2. Moderately vigorous to vigorous growth habit.
3. Dark green-colored leaves.
4. Freely flowering habit.
5. Single light yellow green-colored flowers.
6. Good garden performance.

Plants of the new *Helleborus* differ from plants of the female parent selection in the following characteristics:

1. Plants of the new *Helleborus* have thicker peduncles than plants of the female parent selection.
2. Plants of the new *Helleborus* have light yellow green-colored flowers whereas plants of the female parent selection have white-colored flowers.

Plants of the new *Helleborus* differ from plants of the male parent selection in the following characteristics:

1. Plants of the new *Helleborus* have fewer leaves than plants of the male parent selection.
2. Flowers of plants of the new *Helleborus* are light yellow green in color whereas flowers of plants of the male parent selection are yellowish white in color.

Plants of the new *Helleborus* can be compared to plants of *Helleborus niger* X *Helleborus* x *hybridus* 'COSEH 5600', disclosed in U.S. Plant patent application Ser. No. 16/602,791 filed concurrently. Plants of the new *Helleborus* differ primarily from plants of 'COSEH 5600' in flower color as plants of the new *Helleborus* have light yellow green-colored flowers whereas plants of 'COSEH 5600' have yellow green, white and purple-colored flowers.

Plants of the new *Helleborus* can be compared to plants of *Helleborus niger* X *Helleborus* x *hybridus* 'COSEH 5700', disclosed in U.S. Plant patent application Ser. No. 16/602,738 filed concurrently. Plants of the new *Helleborus* differ primarily from plants of 'COSEH 5700' in flower color as plants of the new *Helleborus* have light yellow green-colored flowers whereas plants of 'COSEH 5700' have red purple-colored flowers.

Plants of the new *Helleborus* can be compared to plants of *Helleborus niger* X *Helleborus* x *hybridus* 'COSEH 5900', disclosed in U.S. Plant patent application Ser. No. 16/602,735 filed concurrently. Plants of the new *Helleborus* differ primarily from plants of 'COSEH 5900' in flower color as plants of the new *Helleborus* have light yellow green-colored flowers whereas plants of 'COSEH 5900' have white-colored flowers. In addition, plants of the new *Helleborus* are not as vigorous as plants of 'COSEH 5900'.

Plants of the new *Helleborus* can be compared to plants of *Helleborus niger* X *Helleborus* x *hybridus* 'COSEH 7100', disclosed in U.S. Plant patent application Ser. No. 16/602,734 filed concurrently. Plants of the new *Helleborus* differ primarily from plants of 'COSEH 7100' in flower color as plants of the new *Helleborus* have light yellow green-colored flowers whereas plants of 'COSEH 7100' have red purple-colored flowers.

Plants of the new *Helleborus* can be compared to plants of *Helleborus niger* X *Helleborus* x *hybridus* 'COSEH 7500', disclosed in U.S. Plant patent application Ser. No. 16/602,737 filed concurrently. Plants of the new *Helleborus* differ primarily from plants of 'COSEH 7500' in flower color as plants of the new *Helleborus* have light yellow green-colored flowers whereas plants of 'COSEH 7500' have white to light yellow green-colored flowers. In addition, plants of the new *Helleborus* are more vigorous than plants of 'COSEH 7500'.

Plants of the new *Helleborus* can also be compared to plants of *Helleborus niger* X *Helleborus* x *hybridus* 'LEM 100', disclosed in U.S. Plant Pat. No. 25,646. In side-by-side comparisons, plants of the new *Helleborus* differ primarily from plants of 'LEM 100' in the following characteristics:

1. Leaves of plants of the new *Helleborus* are lighter green in color than leaves of plants of 'LEM 100'.
2. Flowers of plants of the new *Helleborus* are light yellow green in color whereas flowers of plants of 'LEM 100' are red purple in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 6900' grown in a container.

Figure 2:
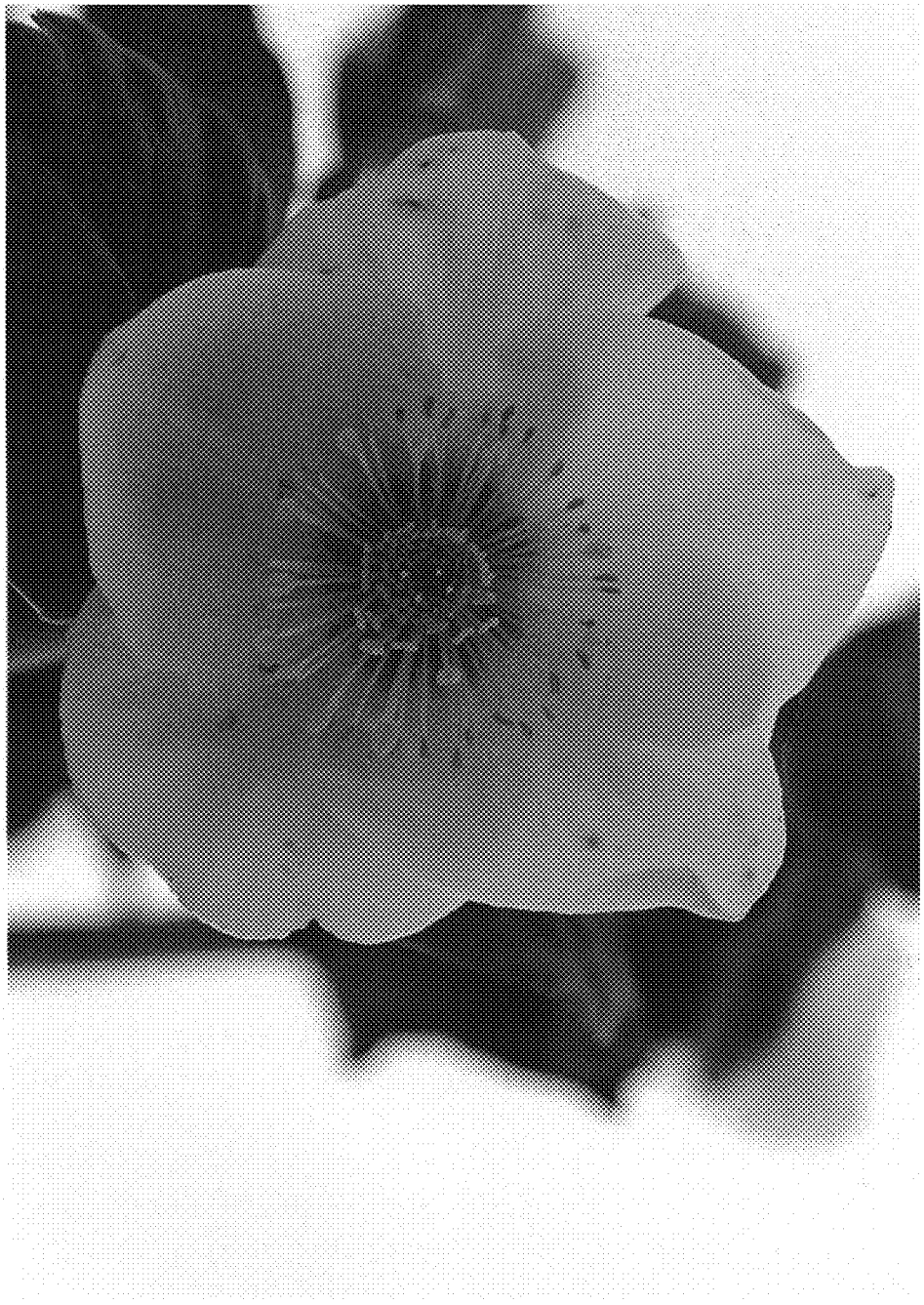

The photograph on the second sheet (FIG. 2 of 2) is a close-up view of a typical flower and leaves of 'COSEH 6900'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 6900'.

Parentage:

*Female, or seed, parent.*—Unnamed selection of *Helleborus niger*, not patented.

*Male, or pollen, parent.*—Unnamed selection of *Helleborus* x *hybridus*, not patented.

Propagation:

*Type.*—In vitro axillary meristem culture.

*Time to initiate roots, winter.*—About 55 days at temperatures about 12° C.

*Time to produce a rooted young plant, winter.*—About 170 days at temperatures ranging from 4° C. to 15° C.

*Root description.*—Thick to thin, fleshy; typically white to brown in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright and mounding plant habit with flowers held within and above the foliar plane; plant shape, roughly flattened globular; moderately vigorous to vigorous growth habit and moderate growth rate.

*Plant height, soil level to top of foliar plane*.—About 27 cm.

*Plant height, soil level to top of flowers*.—About 28.5 cm.

*Plant diameter* (*area of spread*).—About 36 cm.

Leaf description:

*Arrangement*.—Leaves arranged in a basal rosette; leaves palmately compound with typically five leaflets per leaf.

*Leaf length*.—About 13.3 cm.

*Leaf width*.—About 14.2 cm.

*Leaflet length*.—About 9 cm.

*Leaflet width*.—About 5.7 cm.

*Leaf shape*.—Palmate; reniform in outline.

*Leaflet shape*.—Broadly elliptic to broadly ovate and obovate.

*Leaflet apex*.—Broadly acute.

*Leaflet base*.—Attenuate.

*Leaflet margin*.—Deeply serrate; slightly to moderately undulate.

*Leaflet texture and luster, upper surface*.—Smooth, glabrous; leathery; moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to 137A and proximally, close to 183A. Developing leaflets, lower surface: Close to 138B and proximally, tinged with close to 183C. Fully developed leaflets, upper surface: Darker than between NN137A and 147A; venation, close to 144C. Fully developed leaflets, lower surface: Close to 147B; venation, close to 144B to 144C.

*Petioles*.—Length: About 13.7 cm. Diameter: About 6 mm to 7 mm. Strength: Strong. Texture and luster, upper and lower surfaces: Smooth, glabrous; slightly glossy. Color, upper and lower surfaces: Close to 144A and proximally, covered heavily with fine dots, close to 200A.

Flower description:

*Flower shape and habit*.—Single rotate flowers; flowers moderately cupped; arranged solitary or in clusters with about two flowers each; moderately freely flowering habit with about 13 flowers developing per plant; flowers face mostly outwardly to slightly nodding.

*Fragrance*.—None detected.

*Natural flowering season*.—Plants begin flowering about ten months after planting; plants flower from the late autumn into the winter in Germany.

*Flower longevity on the plant*.—About three to four months; sepals persistent, other flower parts are not persistent.

*Flower buds*.—Length: About 2.8 cm. Diameter: About 1.5 cm. Shape: Ovate to narrowly ovate. Texture and luster: Smooth, glabrous; matte. Color: Close to 157A to 157B.

*Inflorescence height*.—About 8.9 cm.

*Inflorescence diameter*.—About 11.2 cm.

*Flower diameter*.—About 8.4 cm by 8.4 cm.

*Flower depth* (*height*).—About 3.8 cm.

*Petals*.—All petals are transformed into nectaries.

*Sepals*.—Quantity and arrangement: About five, arranged in a single whorl. Length: About 5.2 cm. Width: About 5.6 cm. Shape: Reniform to broadly ovate, moderately concave. Apex: Obtuse. Base: Truncate to rounded. Margin: Entire; moderately undulate. Texture and luster, upper and lower surfaces: Smooth, glabrous; matte. Color: When opening, upper and lower surfaces: Close to 155C and proximally, close to 145B; venation, similar to lamina color. Fully opened, upper and lower surfaces: Close to between 150D and 157D, distally, tinged with close to 145D to 145C and proximally, close to 145B; venation, similar to lamina color; with development, close to 145A to 145B and proximally, close to 145A.

*Flower bracts*.—Quantity per flower: Typically one or two. Length: About 7.7 cm. Width: About 5.4 cm. Shape: Broadly ovate. Apex: Broadly acute. Base: Cuneate. Margin: Finely serrate to serrate; not undulate. Color, upper surface: Close to NN137A; venation, similar to lamina. Color, lower surface: Close to 147B; venation, close to 145B.

*Peduncles*.—Length: About 19.1 cm. Diameter: About 1 cm. Aspect: About 15° from vertical. Strength: Strong. Texture and luster: Smooth, glabrous; slightly glossy. Color: Close to 144B to 144C; proximally, moderately to heavily covered with fine dots, close to 184A to 184B.

*Pedicels*.—Length: About 3.8 cm. Diameter: About 4 mm. Aspect: About 10° from peduncle axis. Strength: Moderately strong. Texture and luster: Smooth, glabrous; moderately glossy. Color: Close to 144B to 144C and heavily covered with fine dots, close to 184B and 184C.

*Reproductive organs*.—Stamens: Quantity per flower: About 120. Filament length: About 1.6 cm. Filament color: Close to 157D. Anther shape: Double and broadly reniform; basifixed. Anther size: About 2 mm by 2 mm. Anther color: Close to 150C. Pollen amount: Moderate. Pollen color: Close to 4D. Pistils: Quantity per flower: About four to seven. Pistil length: About 4 mm. Stigma diameter: About 0.3 mm. Stigma shape: Club-shaped. Stigma color: Close to 150D. Style length: About 3 mm. Style color: Close to 185C. Ovary color: Close to 145D. Nectaries (transformed petals): Quantity per flower: About 14. Length: About 1.2 cm. Diameter: About 6 mm. Shape: Tubular, flattened. Texture and luster, inner and outer surfaces: Smooth, glabrous; slightly glossy. Color, immature, inner and outer surfaces: Close to N144A and proximally, close to 144A. Color, mature, inner and outer surfaces: Close to N144A, distally, close to 151B and 151C and proximally, close to 146C; with development, close to N144A and distally, close to 153C and proximally, close to 153C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 6900' as illustrated and described.

* * * * *